United States Patent
Kaplan et al.

(10) Patent No.: US 11,931,136 B2
(45) Date of Patent: Mar. 19, 2024

(54) DEVICE AND METHOD FOR SENSING SIGNALS FROM A BODY

(71) Applicants: Baxter International Inc., Deerfield, IL (US); Baxter Healthcare SA, Glattpark (CH)

(72) Inventors: Yochay Kaplan, RaAnana (IL); Baruch Levy, Lehavim (IL); Eliezer Schusman, RaAnana (IL); Mordechai Dinour, Karney Shomron (IL)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 536 days.

(21) Appl. No.: 16/916,541

(22) Filed: Jun. 30, 2020

(65) Prior Publication Data
US 2021/0000378 A1 Jan. 7, 2021

Related U.S. Application Data (60) Provisional application No. 62/869,069, filed on Jul. 1, 2019.

(51) Int. Cl.
| | |
|---|---|
| *A61B 5/00* | (2006.01) |
| *A61B 5/053* | (2021.01) |
| *A61B 5/0531* | (2021.01) |
| *H01R 12/77* | (2011.01) |
| *H01R 13/64* | (2006.01) |

(52) U.S. Cl.
CPC .......... *A61B 5/0531* (2013.01); *A61B 5/6832* (2013.01); *A61B 5/684* (2013.01);
(Continued)

(58) Field of Classification Search
CPC ....... A61B 5/053; A61B 5/282; A61B 5/0535; A61B 5/0295; A61B 5/684; A61B 5/6832; A61B 5/0531; A61B 5/746; A61B 2562/0217; A61B 2562/222; A61B 2562/08; A61B 2562/227; A61B 2562/0209; A61B 2562/0215; A61B 2562/166
See application file for complete search history.

(56) References Cited

U.S. PATENT DOCUMENTS

| | | | |
|---|---|---|---|
| 4,353,372 A | 10/1982 | Ayer | |
| 2002/0138011 A1* | 9/2002 | Rantala | A61B 5/303 |
| | | | 600/509 |

(Continued)

FOREIGN PATENT DOCUMENTS

| | | |
|---|---|---|
| WO | 2006087696 A2 | 8/2006 |
| WO | 2009022330 A2 | 2/2009 |

OTHER PUBLICATIONS

Preliminary Report on Patentability for related International Application No. PCT/US2020/040233; action dated Dec. 28, 2021; (9 pages).

(Continued)

*Primary Examiner* — Chu Chuan Liu
(74) *Attorney, Agent, or Firm* — K&L Gates LLP (57) ABSTRACT

A device for transmitting and sensing signals comprises a non-conductive substrate adherable to a skin of a subject, two or more electrical contacts printed on the substrate, and a disposable connector, connectable to a compatible cable connector of a cable which receives signals from the contacts via the disposable connector. The disposable connector has a symmetric shape such that mating between the disposable connector and the compatible cable connector is established at either one of two flipped orientations.

19 Claims, 10 Drawing Sheets

(52) U.S. Cl.
CPC ............ *A61B 5/746* (2013.01); *H01R 12/77* (2013.01); *H01R 13/64* (2013.01); *A61B 2562/0215* (2017.08); *A61B 2562/0217* (2017.08); *A61B 2562/08* (2013.01); *A61B 2562/166* (2013.01); *A61B 2562/222* (2013.01); *A61B 2562/227* (2013.01)

(56) References Cited

U.S. PATENT DOCUMENTS

| | | | | |
|---|---|---|---|---|
| 2009/0303001 | A1* | 12/2009 | Brumer ................. | A61B 5/282 340/10.1 |
| 2014/0066741 | A1* | 3/2014 | Peterson ................ | A61B 5/282 600/393 |
| 2014/0073895 | A1* | 3/2014 | Freeman ................ | A61B 5/291 600/382 |

OTHER PUBLICATIONS

International Search Report and Written Opinion for related International Application No. PCT/US2020/040233; action dated Sep. 10, 2020; (16 pages).

* cited by examiner

DEVICE AND METHOD FOR SENSING SIGNALS FROM A BODY

RELATED APPLICATIONS

This application claims the benefit of priority of U.S. Provisional Patent Application No. 62/869,069 filed on Jul. 1, 2019. This application is being filed on the same day with an international patent application entitled "DEVICE AND METHOD FOR SENSING SIGNALS FROM A BODY" claiming the benefit of priority of U.S. Provisional Patent Application No. 62/869,069 filed on Jul. 1, 2019.

The contents of all of the above documents are incorporated by reference as if fully set forth herein.

FIELD AND BACKGROUND OF THE INVENTION

The present invention, in some embodiments thereof, relates to a medical device and, more particularly, but not exclusively, to a device and method for sensing signals, such as, but not limited to, radiofrequency signals from a body.

Technologies related to measurement of electrical properties of organs, such as the measurement of bioimpedance are generally known. Various methods employing bioimpedance are found in: International Publication Nos. WO2004/098376, WO2006/087696, WO2008/102362, WO2009/022330, and WO2010/032252, WO2013/014671, the contents of which are hereby incorporated by reference.

For example, the '696 application discloses transmitting output radiofrequency signals to an organ of a subject, receiving input radiofrequency signals from the organ, determining a phase shift of the input signals relative to the output signals, and using the phase shift to calculate a cardiac output of the subject.

The '362 application describes a sticker for transmitting and sensing the radiofrequency signals. Electrical contacts are fixed at distance therebetween to reduce effects of variable inter-electrode distance on the measurement. The sticker is connected to a monitoring system via a connector having conductive members, wherein each electrical contact is in electrical communication with one conductive member via a different conducting line.

SUMMARY OF THE INVENTION

According to an aspect of some embodiments of the invention there is provided a device for transmitting and sensing signals. The device comprises a non-conductive substrate adherable to a skin of a subject; a first and a second electrical contacts printed on the substrate; a disposable connector, connectable to a compatible cable connector of a cable which receives signals from the contacts via the disposable connector, for transmitting the signals to a signal processor of a system for measuring bioimpedance. The disposable connector has a symmetric shape such that mating between the disposable connector and the compatible cable connector is established at either one of two flipped orientations.

According to some embodiments of the invention the device is packed with a label indicative that the device is for attachment to each of a plurality of different locations of a body of a subject.

According to some embodiments of the invention the plurality of different locations comprises: a ventral upper-left region, a ventral upper-right region, a ventral lower-left region, a ventral lower-right region, a dorsal upper-left region, a dorsal upper-right region, a dorsal lower-left region and a dorsal lower-right region.

According to some embodiments of the invention a length of the device, from the contacts to the disposable connector is less than 25 cm.

According to some embodiments of the invention the disposable connector is attached to an integral extension of the non-conductive substrate, in a manner that the disposable connector and the non-conductive substrate are parallel to each other.

According to some embodiments of the invention the device comprises an authentication tag mounted on, printed on, or integrated with, the disposable connector, the authentication tag being configured for authenticating the device, wherein a combined thickness of the disposable connector and the authentication tag is less than 4 mm.

According to some embodiments of the invention the authentication tag comprises an electronic chip having an internal clock or counter, and is configured to generate an alert signal and transmitting the alert signal over the cable to the system, responsively to a state of the internal clock or counter.

According to an aspect of some embodiments of the present invention there is provided a kit. The kit comprises a plurality of devices for transmitting and sensing signals, wherein all devices are identical in appearance and structure and wherein each device is the device as delineated above and optionally and preferably as further exemplified below.

According to an aspect of some embodiments of the present invention there is provided a kit for transmitting and sensing signals. The kit comprises a plurality of devices for transmitting and sensing signals, wherein each device is the device as delineated above and optionally and preferably as further exemplified below. The kit also comprises a multi-connection cable having a respective plurality of cable connectors at a distal end of the cable, wherein each cable connector is compatible with a disposable connector of one of the devices.

According to some embodiments of the invention for each pair of disposable connector and cable connector of the kit, at least one of the disposable connector and the cable connector comprises a mark indicative of a connection orientation depending on a body section of the subject to which the device is to be attached.

According to some embodiments of the invention all the devices in the kit are identical in appearance and structure.

According to some embodiments of the invention the disposable connector is attached to an integral extension of the non-conductive substrate, in a manner that the disposable connector, the non-conductive substrate, and the cable connector once connected to the disposable connector, are all parallel to each other.

According to some embodiments of the invention there are four devices in the kit.

According to an aspect of some embodiments of the present invention there is provided a method of transmitting and sensing signals. The method comprises attaching to a body of a subject a plurality of devices for transmitting and sensing signals, wherein each device is the device as delineated above and optionally and preferably as further exemplified below. The method comprises connecting a multi-connection cable between the plurality of devices and a connector panel of a bioimpedance measuring system.

According to an aspect of some embodiments of the present invention there is provided a kit for transmitting and sensing signals. The kit comprises a multi-connection cable having a plurality of cable connectors at a distal end of the cable for establishing electrical communication between each of the cable connectors and a signal processor of a system for measuring bioimpedance that is connectable to a proximal end of the cable, and a plurality of devices for transmitting and sensing signals, wherein each device comprises a non-conductive substrate adherable to a skin of a subject, a first and a second electrical contacts printed on the substrate, and a disposable connector. According to some embodiments of the invention each disposable connector is connectable to a compatible cable connector of the cable in a manner that a combined thickness of the disposable connector and the compatible cable connector, once connected, is less than 4 mm.

According to some embodiments of the invention the disposable connector of the kit is orientation-specific, such that mating between the disposable connector and the compatible cable connector is established only at one orientation, but not at a flipped orientation. According to some embodiments of the invention each of the devices of the kit comprises a mark or is packed in a separate package comprising a mark, the mark being indicative of a body section of the subject to which the device is to be attached. According to some embodiments of the invention each cable connector comprises a mark indicative of a device to be connected to the cable connector by a respective disposable connector.

According to some embodiments of the invention the disposable connector has a symmetric shape, such that mating between the disposable connector and the cable connector is established at either one of two flipped orientations. According to some embodiments of the invention at least one of the devices of the kit is packed with a label indicative that the at least one device is for attachment to each of a plurality of different locations of a body of a subject, optionally and preferably an upper part of a body of a subject. According to some embodiments of the invention the plurality of different locations comprises: a ventral upper-left region, a ventral upper-right region, a ventral lower-left region, a ventral lower-right region, a dorsal upper-left region, a dorsal upper-right region, a dorsal lower-left region and a dorsal lower-right region. According to some embodiments of the invention for each pair of disposable connector and cable connector, at least one of the disposable connector and the cable connector comprises a mark indicative of a connection orientation depending on a body section of the subject to which the device is to be attached. According to some embodiments of the invention all devices are identical in appearance and structure. According to some embodiments of the invention there are four devices.

According to some embodiments of the invention a length of each device of the kit, from the contacts to the disposable connector is less than 25 cm.

According to some embodiments of the invention each device of the kit comprises printed conducting lines leading from the contacts to the disposable connector.

According to some embodiments of the invention the disposable connector comprises a first conducting line connected to the first electrical contact, a second conducting line connected to the second electrical contact, and at least one floating conducting line between the first and the second conducting lines.

According to some embodiments of the invention the conducting lines are printed conducting lines.

According to some embodiments of the invention the conducting lines, and the printed electrical contacts engage a same plane.

According to some embodiments of the invention the disposable connector is attached to an integral extension of the non-conductive substrate, in a manner that the disposable connector, the non-conductive substrate, and the cable connector, once connected to the disposable connector, are all parallel to each other.

According to some embodiments of the invention the disposable connector comprises authentication tag for authenticating the respective device, and wherein the thickness of the less than 4 mm encompasses the disposable connector, the authentication tag and the cable connector.

According to some embodiments of the invention authentication tag comprises an electronic chip having an internal clock or counter, and is configured to generate an alert signal and transmitting the alert signal over the cable to the bioimpedance measuring system, responsively to a state of the internal clock or counter.

According to some embodiments of the invention the multi-connection cable comprises separate electric shields for lines conducting a transmit signal and lines conducting a receive signal.

According to an aspect of some embodiments of the present invention there is provided a method of transmitting and sensing signals. The method comprises providing the kit as delineated above and optionally and preferably as further exemplified below; attaching to a skin of a subject the plurality of devices, at a respective plurality of different locations; and connecting the multi-connection cable between the plurality of devices and a connector panel of a system for measuring bioimpedance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to a medical device and, more particularly, but not exclusively, to a device and method for sensing signals, such as, but not limited to, radiofrequency signals from a body.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Methods employing bioimpedance measurement involve placing a plurality of electrodes on a patient's skin, typically in the thoracic region. Electrical signals are transmitted and received via the electrodes, and changes in the electrical impedance of the subject's tissue over time are measured, and correlated with cardiac parameters.

Due to various anatomical factors, the electrodes are typically placed over certain areas of the body to achieve better correlation between measured changes in bioimpedance and cardiac parameters. A typical arrangement for monitoring electrical properties of a body section, is a tetrapolar arrangement of electrodes attached to the skin of the subject at the upper and lower regions of the upper part of the body. Each pair of electrodes is soldered to a distal end of a cable that is connected at its proximal end to a signal processor. The signal processor analyzes the signals received from the electrodes and correlates them with cardiac parameters.

The present inventors found that soldering of the cable to the electrodes can cause a usability issue. For example, during surgery the cable may be detached from the electrodes, resulting in a loss of signal. In such a situation, attaching a new set of electrode is oftentimes not possible since it interrupts the surgery.

The present inventors also found that the wires within the cable are not very immune to external noisy signals and are not immune to cross talk between the transmitting electrode and the receiving electrode. The inventors found that such situation can result in a noisier signal and in a difficulty to detect detachment of the electrode from the skin.

The present inventors also found that bioimpedance measurement can be executed also by connecting the electrodes to a dorsal region of the subject. However, while reducing such connection to practice, it found by the inventors that the electrodes cause discomfort to the subject, in particular when the subject is in supine position, and may also result in pressure sores or other types on injuries.

Figure 1A:
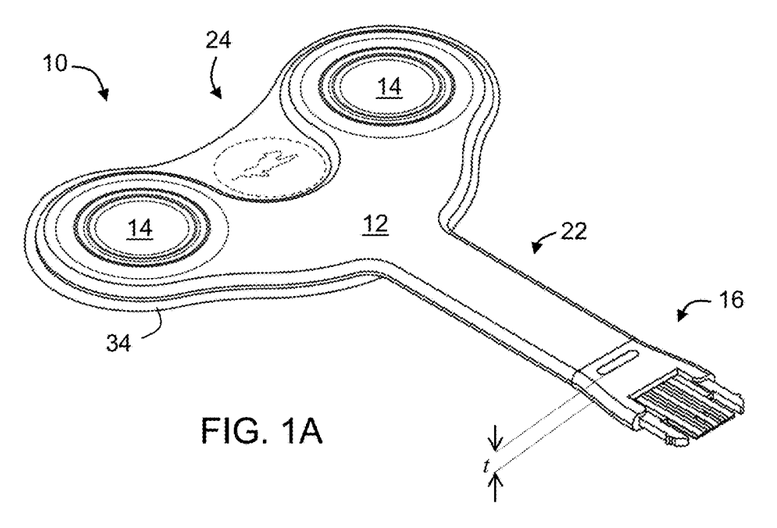
FIGS. 1A-C are schematic illustrations showing a perspective view (FIG. 1A) a front view (FIG. 1B) and a back view (FIG. 1C) of a device for transmitting and sensing signals, according to some embodiments of the present invention.
Figure 1B:
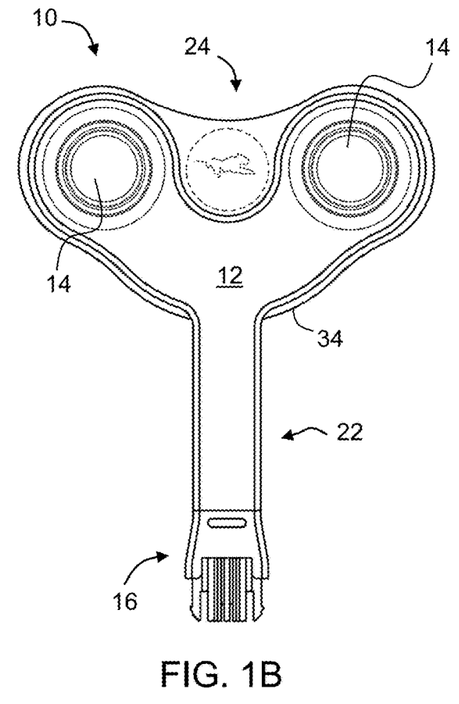
Figure 1C:
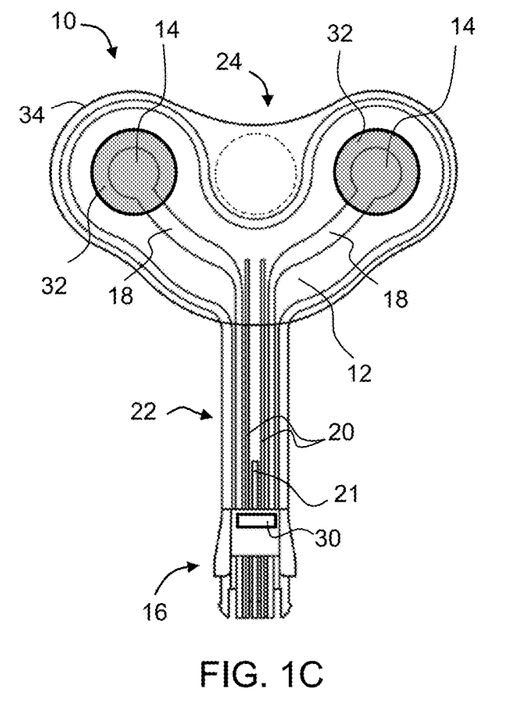

In a search for a solution for at least one of the above problems, the present inventors devised a device and a kit for transmitting and sensing signals. Referring now to the drawings, FIGS. 1A-C are a perspective view (FIG. 1A) a front view (FIG. 1B) and a back view (FIG. 1C) of a device 10 for transmitting and sensing signals, according to some embodiments of the present invention. Device 10 can comprise a non-conductive substrate 12, two electrical contacts 14 printed on substrate 12, and a disposable connector 16. Preferably, device 10 is disposable by its entirety. The back side of substrate 12 is typically adherable to a skin of a subject. For example, the back side of substrate 12 can include an adhesive layer (not shown, see FIGS. 2A-B) for attaching the back side of substrate 12 to the skin of the subject.

Substrate 12 optionally and preferably has a multilayer structure. A representative example of a multiplayer structure suitable for substrate 12 is described below, with reference to FIGS. 2A-B. Connector 16 is typically attached to an integral extension 22 of non-conductive substrate 12, in a manner that connector 16 and substrate 12 are parallel to each other. This improves the comfort to the subject, particularly when the device is between the subject's skin and the bed (e.g., connected to a dorsal region of the subject, while the subject is in supine position). This is unlike conventional electrodes which include a connector that protrudes out of the adherable substrate. Integral extension 22 is optionally and preferably elongated, with a length-to-width aspect ratio of from about 3 to about 10, e.g., about.

In any of the embodiments described herein, the thickness t of connector 16, as measured perpendicularly to the substrate 12 is preferably less than 4 mm. In experiments performed by the inventors it was found that when connector 16 has a thickness of less than 4 mm it is unnoticeable to the majority of the subjects, it does not cause pressure sores or other types on injuries, and therefore significantly improves the comfort to the subject.

Contacts 14 are spaced apart from each other. One of contacts 14 serves for transmitting a transmit signal Tx to the body of the subject and the another one of contacts 14 serves for sensing a receive signal Rx from the body of the subject. A typical distance between the centers of contacts 14 is from about 10 mm to about 70 mm, more preferably from about 20 mm to about 70 mm, more preferably from about 30 mm to about 70 mm, more preferably from about 40 mm to about 70 mm, more preferably from about 50 mm to about 70 mm, more preferably from about 55 mm to about 65 mm, more preferably from about 57 mm to about 62 mm, more preferably from about 57 mm to about 60 mm, or from about 58 mm to about 59 mm, e.g., about 58.5 mm. It was found by the inventors that such range of distances between the point of entry of the Tx signal and the point of exit of the Rx signal provide substantially better results compared to other distances. Contacts 14 are typically printed on a section 24 of substrate 12 from which extension 22 is extending, and which is typically wider than extension 22. Typically, but not necessarily, the length-to-width aspect ratio of section 24 is from about 0.5 to about 1.5. The overall length of device 10, from contacts 14 to connector 16 is typically less than 25 cm or less than 20 cm, e.g., from about 5 cm to about 15 cm. As will be explained below, the use of device 10 includes establishing electrical communication between device 10 and a signal processor via a cable, where device 10 is connected to a cable connector at a distal end of the cable, and the signal processor is connected to a cable connector at a proximal end of the cable. Unlike device 10, the cable, including the connectors at its proximal and distal ends, can typically be used a plurality of times and is therefore not fabricated disposable. Thus, making device 10 sufficiently small (e.g., less than 25 cm or less than 20 cm or less than 15 cm) is advantageous from the standpoint of cost, since in this case a larger portion of the length of the communication between the contacts 14 and the signal processor is by the non-disposable cable, which can be re-used.

In some embodiments of the present invention device comprises boluses 32 of gel covering contacts 14 at the back side of device 10. Boluses 32 serve for providing better electrical contact and impedance matching with the skin of the subject. Boluses 32 can comprise any conductive gel, such as, but not limited to, a conductive hydrogel. In some embodiments of the present invention the back side of device 10 is at least partially covered by a removable protective film 34 for protecting the contacts 14, the boluses 32, and the adhesive layer.

Device 10 also comprises a pair of conducting lines 18 leading from contacts 14 to connector 16. Conducting lines 18 are optionally and preferably also printed on substrate 12. In some embodiments of the present invention device 10 also comprises one or more floating conducting lines 20 between conducting lines 18. The advantage of these embodiments is that floating lines 20 provides electrical shielding between lines 18. Preferably, the floating conducting line(s) 20 is also printed on substrate 12. Conducting lines 18 and 20 (when employed) preferably engage the same plane with electrical contacts 14.

In some embodiments of the present invention device 10 comprises an authentication tag 30 mounted or printed on connector 16, or otherwise integrated therewith. Authentication tag 30 is configured to authenticate device 10 when connected to a bioimpedance measuring system. In any embodiments in which tag 30 is employed, the combined thickness t of connector 16 and tag 30 is preferably less than 4 mm.

Authentication tag 30 can be of any machine-readable type known in the art, such as, but not limited to, a barcode, or an electronic chip, e.g., an RFID chip, EEPROM chip or an RTLS chip. In some embodiments of the present invention the electronic chip of authentication tag 30 comprises an internal clock or counter, and is configured to generate an alert signal, responsively to a state of the internal clock or counter. For example, the electronic chip can optionally and preferably measure the elapsed time from the first use of device 10 and generate an alert signal when the device is in use for a time period which is above a preset time period during which the disposable device 10 is recommended for clinical use (e.g., a preset time period of 30 minutes, or 1 hour, or 2 hours, or 6 hours or 12 hours or 24 hours or 48 hours, etc.). In response to the alert signal, the operator can replace the device. When authentication tag 30 comprises electronic chip, device 10 optionally and preferably comprises a dedicated authentication conducting line 21 for transmitting signals (e.g., authentication signal, clock signal, alert signal, etc.) to the signal processor. Preferably, authentication line 21 is also printed on substrate 12, and preferably engages the same plane with lines 18 and 20 (when employed) and with electrical contacts 14.

Figure 2A:
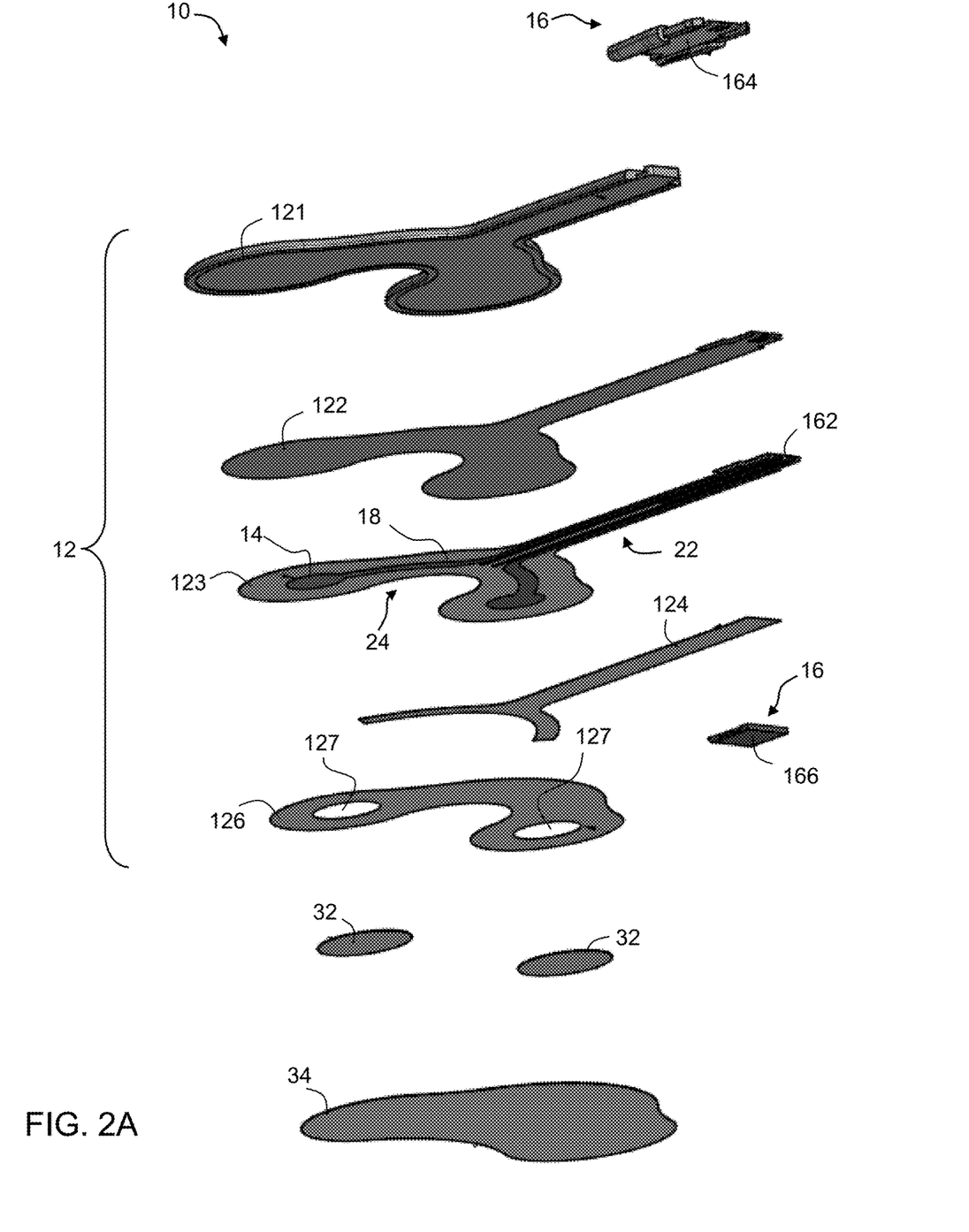
FIG. 2A is a schematic illustration showing an exploded view of a device for transmitting and sensing signals, according to some embodiments of the present invention.

FIG. 2A is a schematic illustration showing an exploded view of device 10, and a method of fabricating device 10, according to some embodiments of the present invention. In some optional embodiments of the present invention substrate 12 is a multilayer substrate. Contacts 14, lines 18 and optionally also lines 20 are printed on an inner layer 123 of substrate 12, preferably using a silver-containing conducting ink. A printed circuit board 162 of connector 16 is attached to the inner layer 123 at the elongated extension 22 of substrate 12. Printed circuit board 162 is at or close to the end of extension 22 that is opposite to section 24. Printed circuit board 162 serves as a carrier substrate for the electronic elements of connector 16 (e.g., conductive terminals, connector contacts, elements of the authentication tag, if included, etc.). Printed circuit board 162 is optionally and preferably made of a thermoplastic polymer, such as, but not limited to, polyethylene terephthalate, polyethylene naphthalate, polybutylene terephthalate, polytrimethylene terephthalate, polycyclohexylene terephthalate, and the like.

Substrate 12 can also comprise a cover 121 that is attached to inner layer 123 by an adhesive layer 122. Cover 121 is non-conductive, and can be made, for example, from a non-conductive polymeric material, such as, but not limited to, a thermoplastic elastomer. Preferably, cover 121 is flexible and has a Shore A hardness of from about 20 to about 50. An isolation layer 124 is attached to inner layer, opposite to cover 121 and adhesive layer 122. Isolation layer 124 is shaped to cover conducting lines 18 and 20. An additional adhesive layer 126, is applied to isolation layer 124, and section 24 of inner layer 123. Adhesive layer 126 has openings 127 that expose contacts 14. Boluses 32 are then applied to adhesive layer 126 to cover openings 127 hence also contacts 14, and removable protective film 34 is attached to adhesive layer 126 for protecting the contacts 14, the boluses 32, and the adhesive layer 126.

A pair of non-conductive connection members 164, 166 of connector 16 are above and below printed circuit board 162. Connection members 164, 166 are shape-wise and size-wise compatible with a cable connector (not shown, see FIGS. 3A and 3B) thereby making device 10 connectable to the cable, by means of connector 16. Connection members 164, 166 are optionally and preferably made of a thermoplastic polymer which is harder than the printed circuit board 162. Representative examples for polymers suitable for connection members 164, 166 including, without limitation, acrylonitrile butadiene styrene, polyacetals, polycarbonates, etc.

Figure 2B:
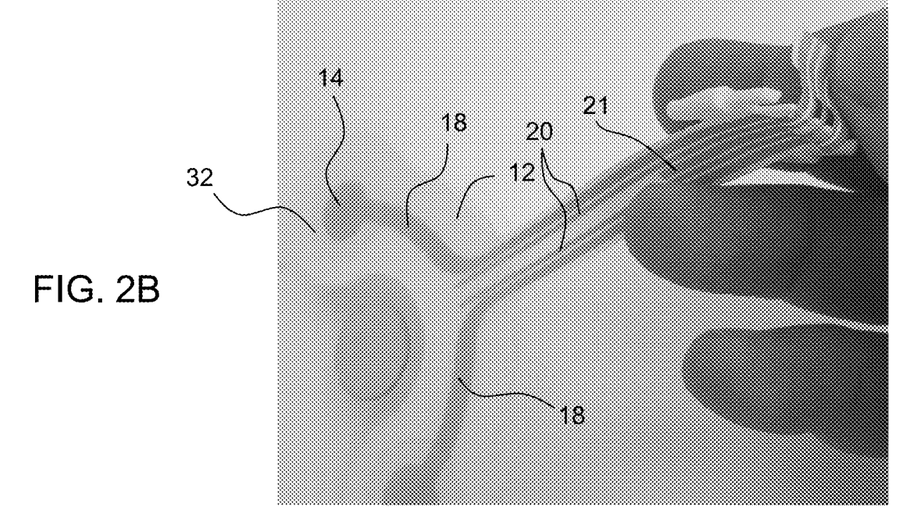
FIG. 2B is an image showing folding of conducting lines on a connection member, according to some embodiments of the present invention.

Printed circuit board 162, and connection members 164, 166 can be mounted either at the end of extension 22 or offset from said end. Connection at the end of extension 22 is useful when it is desired to make connector 16 a single-sided connector in which the conductive lines are only at one side of connector 16. Connection offset the end of extension 22 is useful when it is desired to make connector 16 a double-sided connector in which the conductive lines are at both sides of connector 16. In the latter embodiments, following the mounting of one or more of the connection members 164, 166, the inner layer 123 with the conductive lines 18 is folded over the respective connection member. An image showing such folding is shown in FIG. 2B.

Figure 3A:
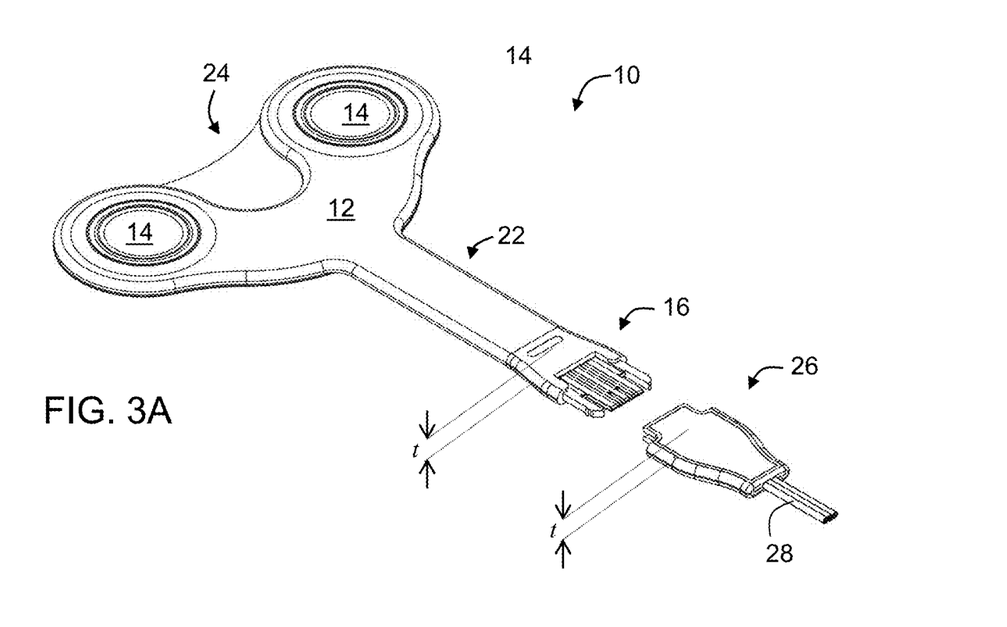
FIGS. 3A and 3B are schematic illustrations showing connection between a connector and a cable by means of a cable connector, according to some embodiments of the present invention.
Figure 3B:
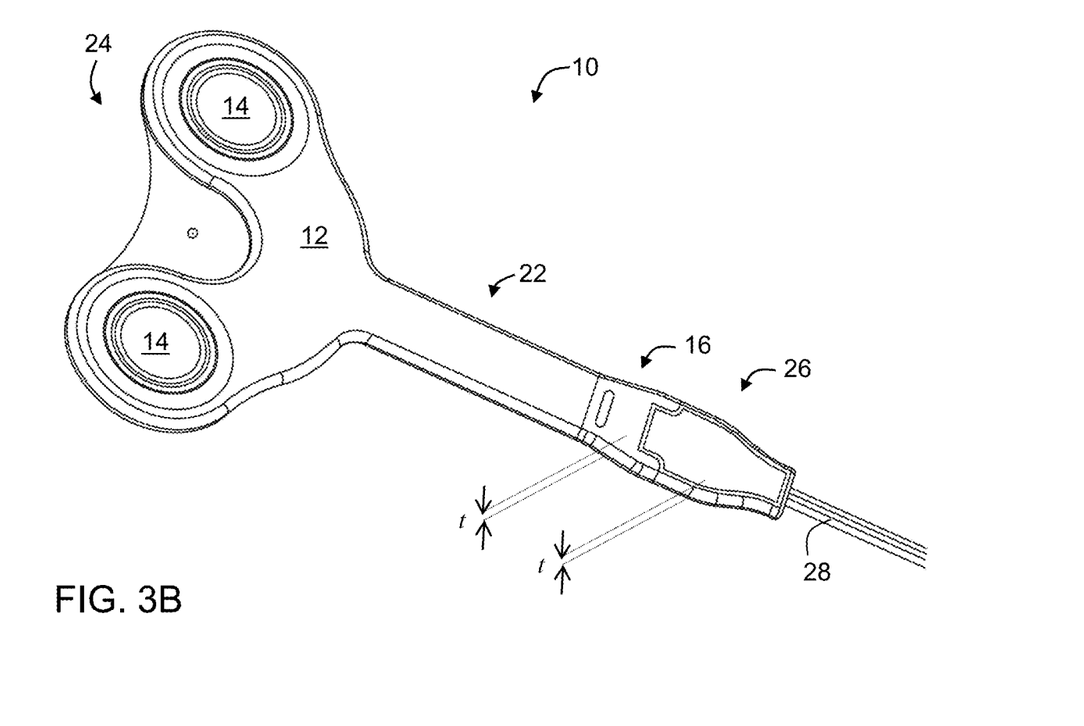

As stated, in use of device 10 an electrical communication is established between device 10 and a data processor via a cable. FIGS. 3A and 3B are schematic illustrations showing connection between connector 16 and a cable 28 by means of a cable connector 26, according to some embodiments of the present invention for establishing such a connection. Since cable connector 26 is typically at the distal end of cable 28, connector 26 is interchangeably referred to herein as distal cable connector 26. Connector 16 is made compatible in terms of size, structure, and function with distal cable connector 26, so as to allow them to mate and establish electrical communication therebetween. Shown in FIGS. 3A and 3B are connectors 16 and 26 in a disconnected (FIG. 3A) and a connected (FIG. 3B) state. While FIGS. 3A and 3B schematically illustrate a configuration in which connector 16 is a male connector and connector 26 is a female connector, configurations in which connector 16 is a female connector and connector 26 is a male connector are also contemplated.

Cable 28 receives a transmit signal Tx from a signal generator (not shown) and transmits this signal to one of contacts 14 via connector 16. Cable 28 also receives a receive signal Rx from another one of contacts 14 via connector 16 and transmits these signals to a signal processor (not shown). In embodiments in which device 10 comprises tag 30, and in which tag 30 comprises an electronic chip, an authentication signal generated by tag 30 can be transmitted over cable 28 to the signal processor.

In any of the embodiments described herein, the combined thickness t of connector 16 and cable connector 26, once connected, is optionally and preferably less than 4 mm. This allows connector 26 to be also between the subject and the bed (when the subject is in supine position and device 10 is connected to the subject's dorsal region), without causing discomfort to the subject, unlike conventional systems. When device 10 comprises authentication tag 30, the aforementioned thickness of less than 4 mm also encompasses authentication tag 30.

Figure 4A:
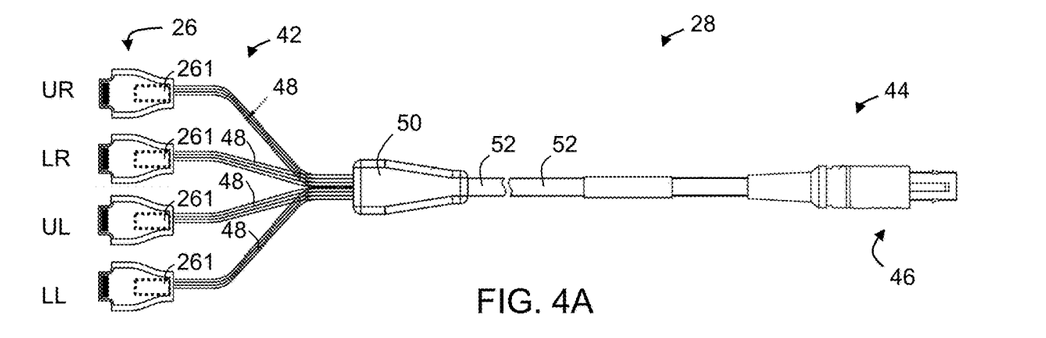
FIGS. 4A and 4B are schematic illustration of a multi-connection cable, in embodiments in which the cable comprises four cable connectors.
Figure 4B:
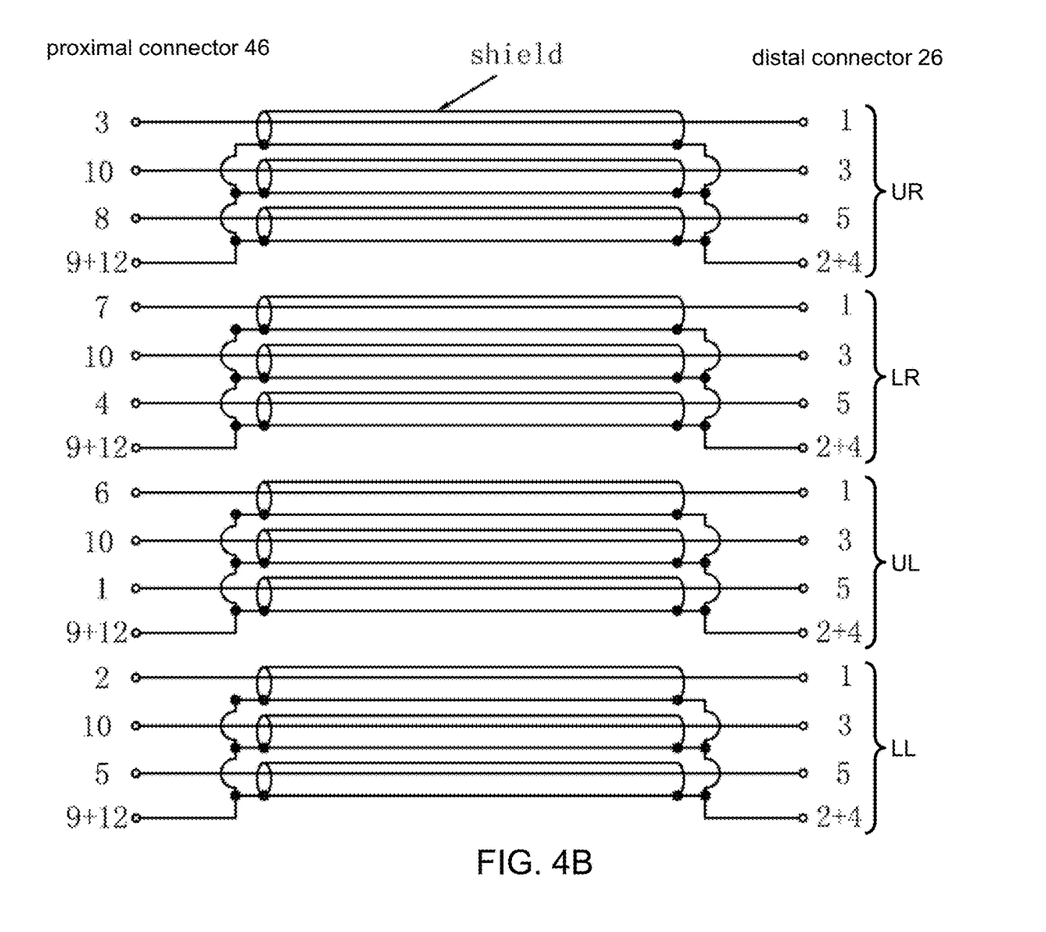

Cable 28 is preferably a multi-connection cable having a plurality of cable connectors 26 at a distal end of cable 28, allowing connecting a respective plurality of devices such as device 10 to cable 28. FIGS. 4A and 4B are schematic illustration of multi-connection cable 28, in embodiments in which cable 28 comprises at its distal end 42 four cable connectors 26, designated UR, LR, UL, and LL, each designated for connection to a disposable connector 16 attached to a different part of the subject's body (e.g., the upper-right, lower-right, upper-left and lower-left regions of the upper part of the body, respectively). It is appreciated that cable 28 can include any number of connectors at its distal end 42, as desired, depending on the number of devices that are to be connected to cable 28. The proximal end 44 of cable 28 comprises a proximal connector 46 that is compatible with a connector panel of a signal processor (not shown).

Each of connectors 26 is connected, for example, by means of a dedicated printed circuit board 261 within connector 26, to a braid 48 of conductive lines and all the braids 48 are joined in a braid joiner 50 to form a combined braid 52 that connects to proximal connector 46. In some embodiments of the present invention one or more of the conductive lines in braid 52 are shielded. Preferably, different conductive lines, e.g., lines conducting a transmit signal Tx and lines conducting a receive signal Rx are shielded by separate electric shields. In various exemplary embodiments of the invention the conductive lines in combined braid 52 are arranged so as to establish electrical communications between each of the distal connectors 26 and the proximal connector 46 according to a connection scheme that is specific to the respective distal connector, that is different from connection schemes of the other distal connectors, and that ensures that Tx and Rx signals flowing through different conducting lines are separated from each other at proximal connector 46.

A representative and non-limiting example of connection schemes between connectors 26 and 46 is schematically illustrated in FIG. 4B. In this example, each cable connector 26 is a five-pin connector, optionally and preferably a linear five-pin connector. The pins of connector 26 are enumerated serially from 1 to 5, where, in the present example, pin Nos. 2 and 4 are combined and serve for shielding, so that each braid 48 is a four-wire braid. Typically, when connector 16 is connected to connector 26, electrical communication is established between floating lines 20 of device 10 and pin Nos. 2 and 4 of connector 26. Each of the conducting lines of braids 48 and 52 that is connected to one of pins 1, 3 and 5 of distal connector 26 is shielded by a shield that is spaced apart from the other shields. The shielding lines within braids 48 and 52 (connected to pins 2 and 4, in present example) can be shorted among all the distal connectors.

Of the non-shielding pins 1, 3 and 5, one communicates a Tx signal and one communicates an Rx signal. For example, the conducting lines in braids 48 and 52 that are connected to pin 1 can communicate Tx signals, the conducting lines braids 48 and 52 that are connected to pin 5 can communicate Rx signals, and all the conducting lines braids 48 and 52 that are connected to pin 3 can serve for authentication. In this case, when connector 16 is connected to connector 26, two separate electrical communications are respectively established between conducting lines 18 of device 10 and pin Nos. 1 and 5 of connector 26, and an additional separate electrical communication is established between authentication line 21 of device 10 and pin No. 3 of connector 26. The authentication lines of braids 48 and 52 (connected to pin No. 3 of connector 26, in the present example) can be shorted among the braids. Shortenings (among the shielding lines, and/or among the authentication lines) can be at proximal connector 46 or, more preferably at braid joiner 50, thus reducing the number of conducting lines in braid 52.

In the illustrated non-limiting example of FIG. 4B, proximal connector 46 comprises 12 pins, enumerated 1 through 12, where, pin Nos. 9 and 12 are combined and serve for shielding. The connection schemes are different from each other in the sense that the Tx and Rx signals of different for each distal connector 26, are communicated via different pins of proximal connector 46. In the present example, the Tx and Rx signals of connector UR are communicated via pin Nos. 3 and 8 of proximal connector 46, the Tx and Rx signals of connector LR are communicated via pin Nos. 7 and 4 of proximal connector 46, the Tx and Rx signals of connector UL are communicated via pin Nos. 6 and 1 of proximal connector 46, and the Tx and Rx signals of connector LL are communicated via pin Nos. 2 and 5 of proximal connector 46.

The present embodiments contemplate one of two scenarios for connecting between connector 16 of device 10 and distal connector 26 of cable 28.

In a first scenario, connector 16 is orientation-specific, such that mating between connectors 16 and 26 is established only at one orientation, but not at a flipped orientation. This can be ensured by making the connectors 16 and 26 non symmetric with respect to a 180° flip, so that when one of connectors 16 and 26 is flipped relative to the proper orientation for connection, the operator will not be able to mate connectors 16 and 26 even if they are laterally aligned. Alternatively, connector 16 can be single-sided with electrical contacts only on one of its front and back sides, so that when one of connectors 16 and 26 is flipped relative to the proper orientation for connection, the operator is able to mate connectors 16 and 26, but no electrical communication is established. The advantage of the first scenario is that it prevents human error with respect to the connections between connectors 16 and 26. In the first scenario, the arrangement of conductive lines 18 of each of devices 10 is specific to the body section to which the respective device is to be attached.

Figure 5A:
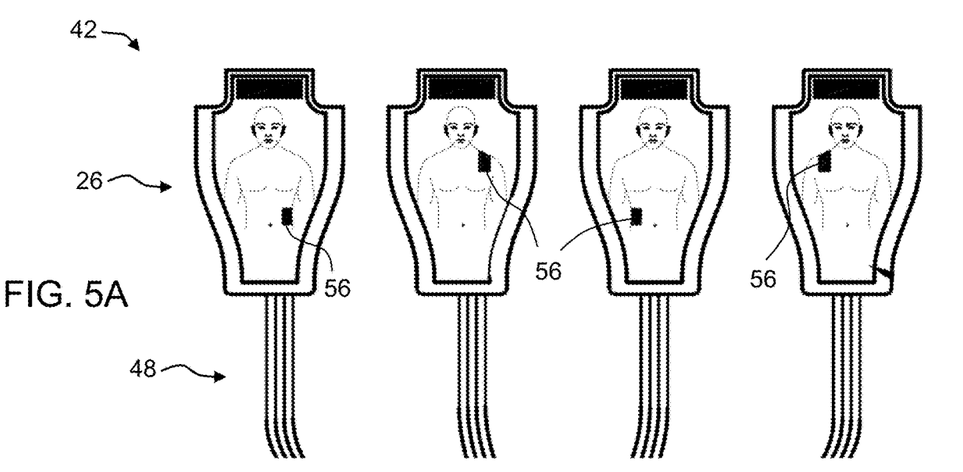
FIG. 5A is a schematic illustration of a distal end of the cable, in embodiments in which on each of the cable connectors, there is a mark indicative of a different body section of the subject.
Figure 5B:
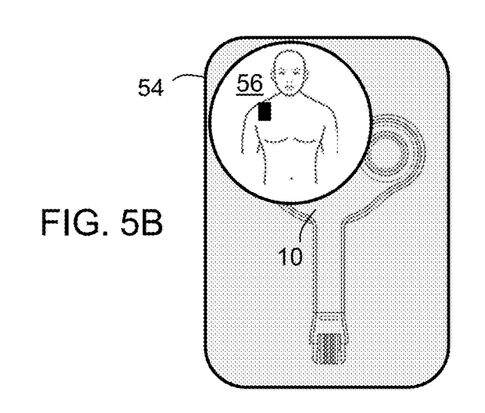
FIGS. 5B-E illustrate a plurality of packages of a device with marks that allow the practitioner to attach each device to its proper location and connect it to the proper distal cable connector.
Figure 5C:
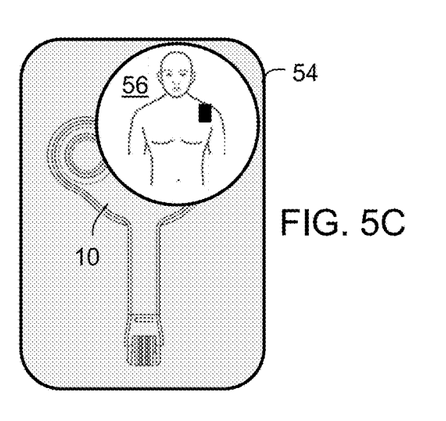
Figure 5D:
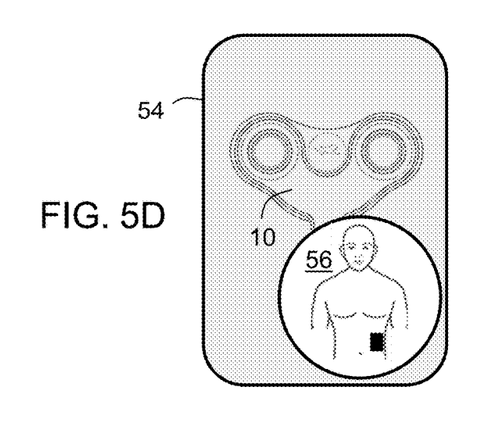
Figure 5E:
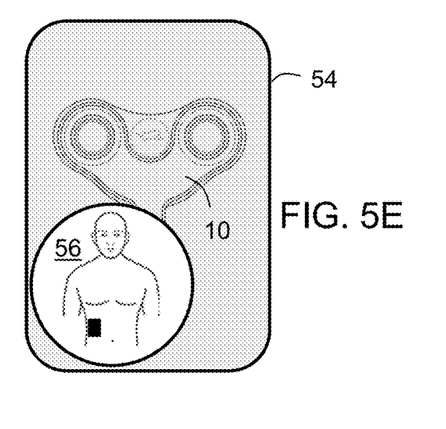

To help the user properly place each of the devices 10 on the subject's body and connect it to the proper cable connector 26 in the first scenario, visual assistance, such as a mark on the respective device, or on a package containing the respective device, may be displayed. The mark can be indicative of a body section to which the device is to be attached. In these embodiments, such or a similar mark is optionally and preferably provided also on the cable connector 26 that is to be connected to the respective device, once attached to the respective body section. A representative example of such visual assistance is schematically illustrated in FIGS. 5A-E. FIG. 5A illustrates the distal end 42 of cable 28, where on each of the distal cable connectors 26 (four cable connectors, in the present example), there is a mark 56 indicative of a different body section of the subject. FIGS. 5B-E illustrate a plurality of packages 54 of device 10 (four packages, in the present example), with marks 56 similar to the marks on distal cable connectors 26, allowing the practitioner to attach each device 10 to its proper location and also connect it to the proper distal cable connector.

In a second scenario, connector 16 has a symmetric shape such that mating between connectors 16 and 26 can be established at either one of two flipped orientations. In these embodiments, connector 16 is made double-sided with electrical contacts on both its front and back sides, so that electrical communication is established for any of the two flipped orientations of connectors 16 and 26 relative to each other. For example, a flipped orientation can correspond to switching between the lines in cable 28 that communicate the Rx and Tx signal, so that one orientation can be used when the device is attached to the dorsal side of the body, while the flipped orientation can be used when the device is attached to the ventral side of the body. The connection schemes described above with respect to FIG. 4B exemplify such a switching (e.g., corresponding to a switch between pin Nos. 1 and 5 of distal connector 26).

The advantage of the second scenario is that it is not required to make the devices 10 specific to the body sections to which they are to be attached. Thus, in the second scenario, all the devices 10 that are included a kit for use in bioimpedance measurement can be identical in shape, size and arrangement of the conducting lines.

Figure 6A:
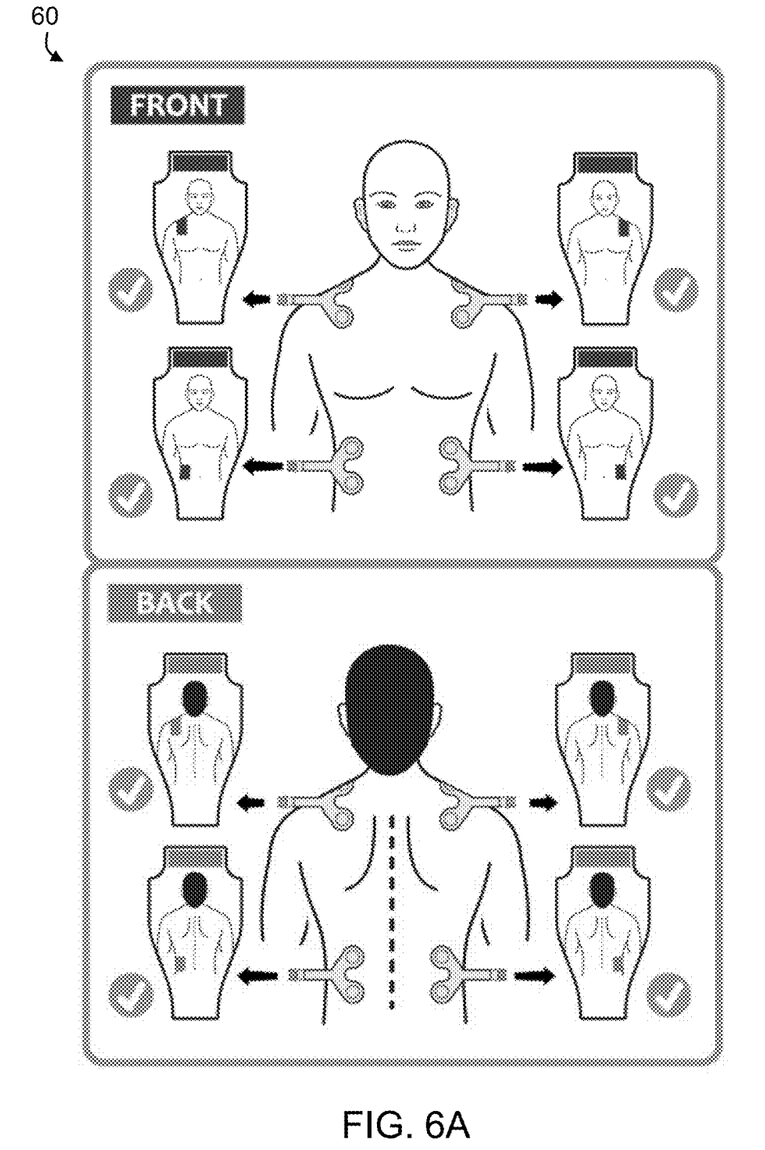
FIG. 6A is a schematic illustration of a label showing eight different locations, on a subject's body, according to various exemplary embodiments of the present invention.

In the second aspect, device 10 can be packed with a label indicative that the device is for attachment to each of a plurality of different locations on the body of the subject, more preferably the upper part of the body of the subject. FIG. 6A illustrate an exemplary label showing eight such different locations, including, without limitation, a ventral upper-left region, a ventral upper-right region, a ventral lower-left region, a ventral lower-right region, a dorsal upper-left region, a dorsal upper-right region, a dorsal lower-left region and a dorsal lower-right region. In these embodiments, each of the distal connectors 26 is optionally and preferably marked with two marks indicative of the proper body section to which the distal connector is intended, for each of its two orientations.

Figure 6B:
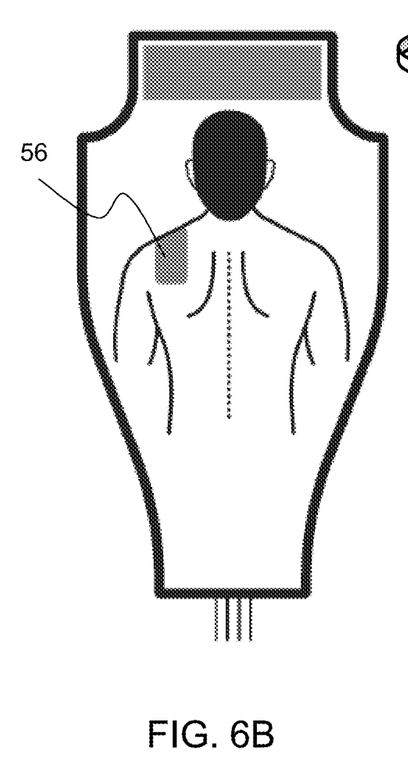
FIGS. 6B and 6C are schematic illustrations of two of the eight possible marks that can be provided on the front and back side of a cable connector, according to some embodiments of the present invention.
Figure 6C:
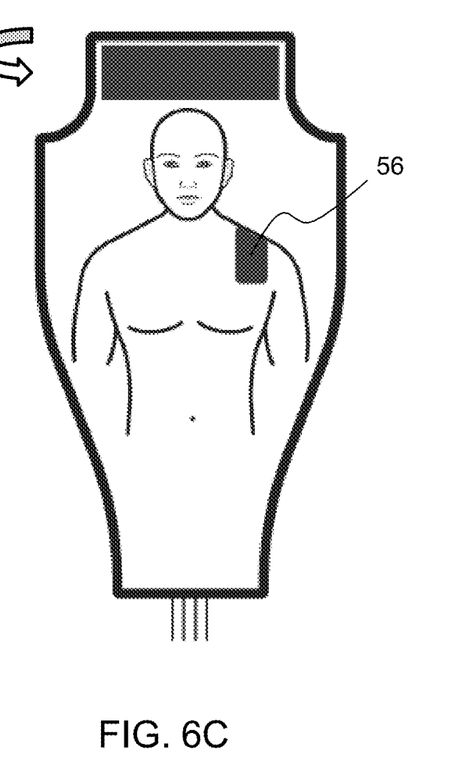

A representative example of two of the eight possible marks 56 is illustrated in FIGS. 6B and 6C. The marks 56 shown in FIGS. 6B and 6C can be provided on the front and back side of the same distal connector 26. FIG. 6B illustrates a mark indicating that the respective orientation is suitable for connecting the respective distal connector 26 to a device 10 that is attached to a dorsal upper-left region, and FIG. 6C illustrates a mark indicating that the respective orientation is suitable for connecting the respective distal connector 26 to a device 10 that is attached to the ventral upper-left region. The ordinarily skilled person, provided with the details described herein would know how to provide marks to the other distal connectors.

Figure 7:
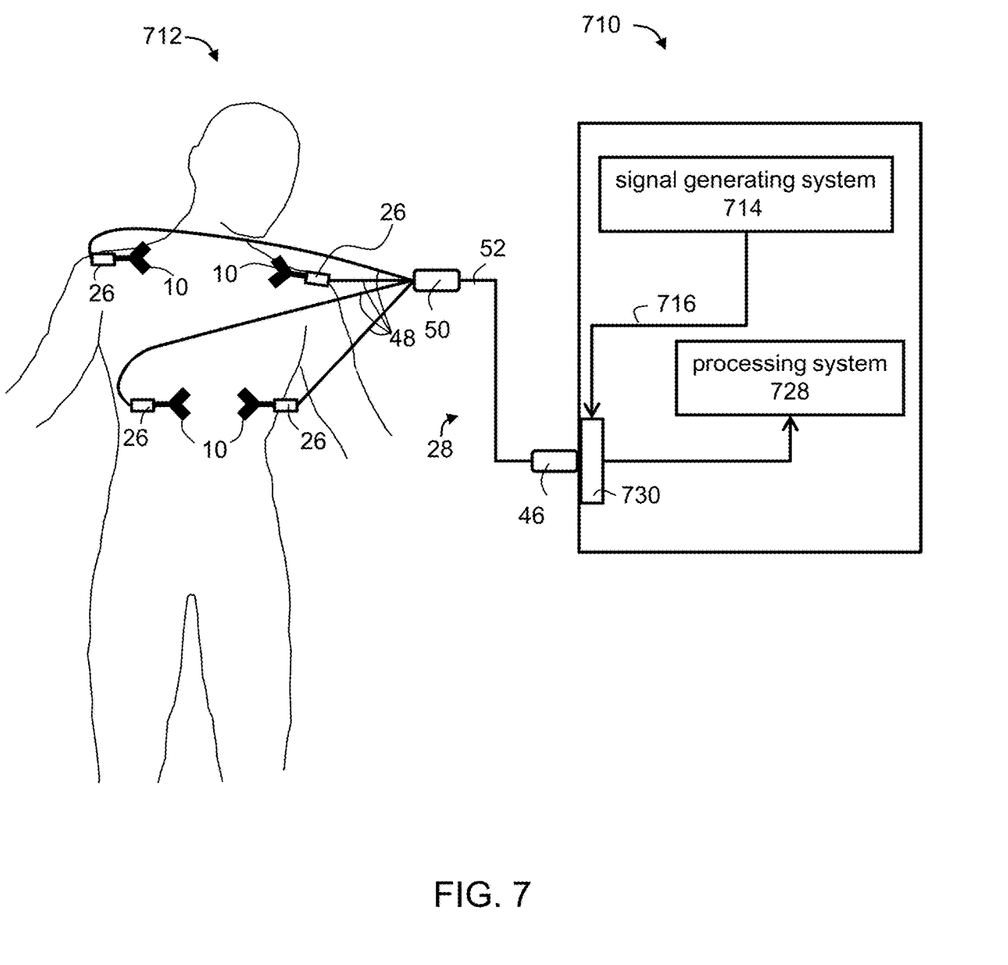
FIG. 7 is a schematic block diagram illustrating a bioimpedance measuring system, according to some embodiments of the present invention.

FIG. 7 is a schematic block diagram illustrating a bioimpedance measuring system 710, according to some embodiments of the present invention. System 710 typically comprises a signal generating system 714, a signal processing system 728 and a connector panel 730. Proximal connector 46 of multi-connection cable 28 is connected to control panel 730. The distal connections 26 of cable 28 are connected to a plurality of devices 10 that are attached to the body of a subject 713. Signal generating system 714 provides one or more output electric Tx signals 716 and transmits the Tx signal 716 to connector panel 730. Connector panel 730 transmits the signal via cable 28 to devices 10. Devices 10 sense one or more input electrical signal Rx 736 and transmit the Rx signal to connector panel 730 via cable 28. Panel 730 transmit the Rx signal 736 to processing system 728.

Processing system 728 serves for providing monitoring information pertaining to the hemodynamic state of the subject. System 728 receives the signals, processes the signals and generates an output pertaining to the processed signals. Preferably, the output is a graphical output, which is transmitted to a computer readable medium, such as a display card, a network card or memory medium of a computer. From the computer readable medium the output can be read by a local or remote computer and displayed, e.g., on a display device. Properties pertaining to the hemodynamics of the subject can be calculated based on the Rx signal using any technique known in the art, such as, but not limited to, the technique disclosed in International Publication Nos. WO2004/098376, WO2006/087696, WO2008/129535, WO2009/022330 and WO2010/032252 the contents of which are hereby incorporated by reference. Representative examples of properties that can be calculated according to some embodiments of the present invention include, stroke volume (SV), cardiac output (CO), ventricular ejection time (VET), cardiac index (CI), thoracic fluid content (TFC), total peripheral resistance index (TPRI), blood vessel compliance and any combination thereof. Optionally and preferably processing system 728 performs the processing in a digital manner. In these embodiments, processing system 728 can comprise an analog to digital converter and a digital data processor or a digital signal processor.

The signals provided by generating system 714 are preferable alternate current (AC) signals which can be at any frequency. It was found by the present inventors that radiofrequency signals are useful, but it is not intended to limit the scope of the present invention to any particular frequency. Specifically, the frequency of the transmitted signals can be below the radiofrequency range, within the radiofrequency range or above the radiofrequency range. A representative frequency range suitable for the present embodiments include, without limitation, from 20 KHz to 800 KHz, e.g., about 75 KHz. Current, generated by the signal generating system of the present embodiments, flows across the organ and causes a voltage drop due to the impedance of the body. The input radiofrequency signals are typically, but not obligatorily, relate to the impedance of an organ of the subject. In various exemplary embodiments of the invention the parameters (e.g., frequency, amplitude, phase) of the output signal(s) is selected such that the input signal is indicative of the impedance of the organ.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Figure 8A:
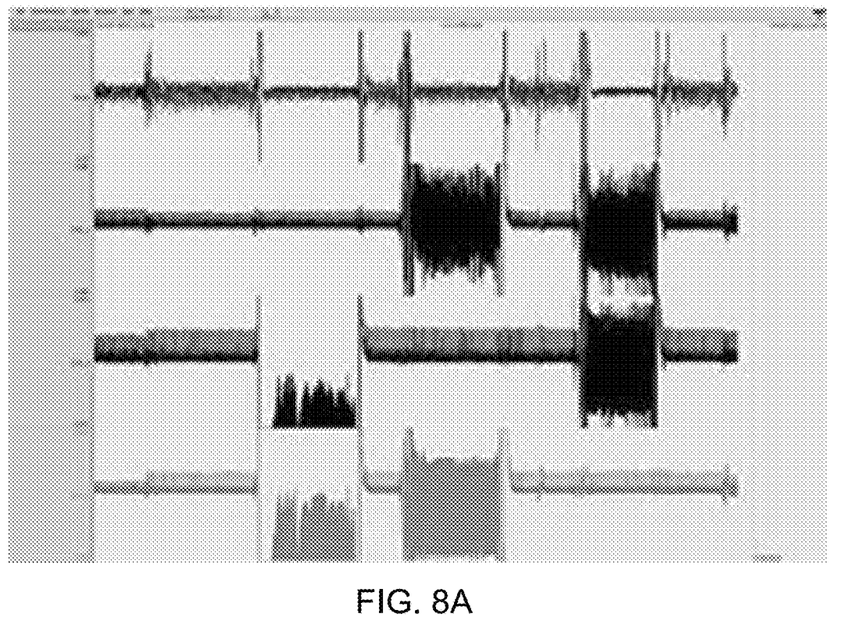
FIGS. 8A and 8B show results of experiments conducted according to some exemplary embodiments of the present invention, to investigate the ability of the device and cable of the present embodiments to reduce cross talk and noise.
Figure 8B:
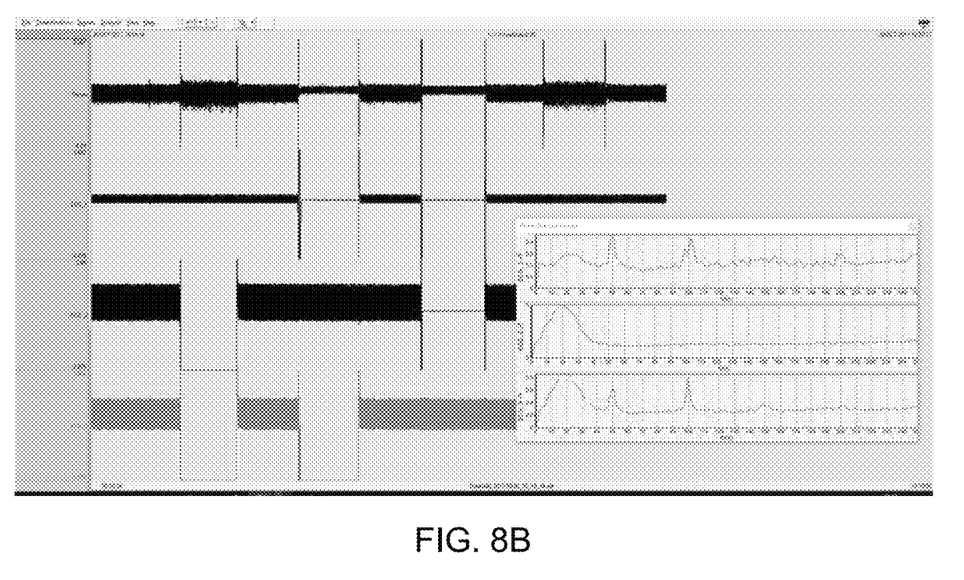

Experiments were executed to investigate the ability of device 10 and cable 28 of the present embodiments to reduce cross talk and noise. The experiments included measuring the Rx signal during detachment of one of the leads. The results are shown in FIGS. 8A and 8B, where FIG. 8A shows signal received using conventional electrodes, and FIG. 8B shows the signal received using device 10 of the present embodiments. As shown in FIG. 8A even after the detachment of one of the leads, the electrode still picks up a signal, demonstrating cross talk between the wires leading from the electrodes to the signal processor. In distinction, FIG. 8B shows that no signal is received after the detachment, demonstrating no cross talk within device 10 and cable 28.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device for transmitting and sensing signals, the device comprising:
   a non-conductive substrate configured to be adhered to a skin of a subject;
   a first and a second electrical contacts printed on said substrate;
   a disposable connector, configured to be connected to a compatible cable connector of a cable receiving signals from said contacts via said disposable connector for transmitting the signals to a system for measuring bioimpedance, said disposable connector having a symmetric shape such that mating between said disposable connector and said compatible cable connector is established at either one of two flipped orientations; and
   an authentication tag mounted on, printed on, or integrated with, said disposable connector and an authentication line for transmitting signals from the authentication tag to a processor including at least an alert indicating that the device needs to be replaced, wherein the authentication line is a dedicated conducting line disposed between a first conducting line and a second conducting line.

2. The device according to claim 1, further comprising a label indicative that the device is for attachment to each of eight different locations of an upper part of a body of a subject.

3. The device of claim 2, wherein said eight different locations comprise: a ventral upper-left region, a ventral upper-right region, a ventral lower-left region, a ventral lower-right region, a dorsal upper-left region, a dorsal upper-right region, a dorsal lower- left region and a dorsal lower-right region.

4. The device of claim 1, wherein a length of the device, from said contacts to said disposable connector is less than 25 cm.

5. The device according to claim 4, comprising printed conducting lines leading from said contacts to said disposable connector.

6. The device according to claim 1, wherein said disposable connector comprises the first conducting line connected to said first electrical contact, the second conducting line connected to said second electrical contact, and at least one floating conducting line between said first and said second conducting lines.

7. The device according to claim 6, wherein said conducting lines are printed conducting lines.

8. The device according to claim 6, wherein said conducting lines, and said printed electrical contacts engage a same plane.

9. The device according to claim 1, wherein said disposable connector is attached to an integral extension of said non-conductive substrate, in a manner that said disposable connector and said non-conductive substrate are parallel to each other.

10. The device according to claim 1, wherein said authentication tag is configured for authenticating the device, wherein a combined thickness of said disposable connector and said authentication tag is less than 4 mm.

11. The device according to claim 10, wherein said authentication tag comprises an electronic chip having an internal clock or counter, and is configured to generate an alert signal and transmitting said alert signal over said cable to said system, responsively to a state of said internal clock or counter.

12. The device according to claim 1, wherein said cable includes a plurality of separate electric shields for lines conducting a transmit signal and lines conducting a receive signal.

13. The device according to claim 1, wherein at least one of the disposable connector and said cable includes a mark indicative of a connection orientation.

14. The device according to claim 1, wherein said cable is a multi-connection cable.

15. A method of transmitting and sensing signals, the method comprising:
   attaching to a body of a subject a plurality of devices for transmitting and sensing signals, a plurality of devices, wherein each device includes
      a non-conductive substrate configured to be adhered to a skin of a subject;
      a first and a second electrical contacts printed on said substrate;
      a disposable connector, configured to be connected to a compatible cable connector of a cable receiving signals from said contacts via said disposable connector for transmitting the signals to a system for measuring bioimpedance, said disposable connector having a symmetric shape such that mating between said disposable connector and said compatible cable connector is established at either one of two flipped orientations; and
      an authentication tag mounted on, printed on, or integrated with, said disposable connector and an authentication line for transmitting signals from the authentication tag to a processor including at least an alert indicating that the device needs to be replaced, wherein the authentication line is a dedicated conducting line disposed between a first conducting line and a second conducting line;
   connecting a multi-connection cable between said plurality of devices and a connector panel of a bioimpedance measuring system.

16. The method of claim 15, wherein each device is configured for attachment to each of eight different locations of an upper part of a body of a subject.

17. The method of claim 16, wherein said eight different locations comprise: a ventral upper-left region, a ventral upper-right region, a ventral lower-left region, a ventral lower-right region, a dorsal upper-left region, a dorsal upper-right region, a dorsal lower- left region and a dorsal lower-right region.

18. The method of claim 15, wherein a length of each device, from said contacts to said disposable connector is less than 25 cm.

19. The method of claim 18, comprising printed conducting lines leading from said contacts to said disposable connector.

* * * * *